(12) United States Patent
Masaki

(10) Patent No.: US 7,478,909 B2
(45) Date of Patent: Jan. 20, 2009

(54) OPTHALMOLOGIC APPARATUS

(75) Inventor: Toshifumi Masaki, Tochigi (JP)

(73) Assignee: Canon Kabushiki Kaisha, Tokyo (JP)

( * ) Notice: Subject to any disclaimer, the term of this patent is extended or adjusted under 35 U.S.C. 154(b) by 314 days.

(21) Appl. No.: 10/772,078

(22) Filed: Feb. 3, 2004

(65) Prior Publication Data

US 2004/0156019 A1    Aug. 12, 2004

(30) Foreign Application Priority Data

Feb. 3, 2003  (JP)  ............................. 2003-025987
Feb. 3, 2003  (JP)  ............................. 2003-025988
Feb. 6, 2003  (JP)  ............................. 2003-029074

(51) Int. Cl.
*A61B 3/14*    (2006.01)

(52) U.S. Cl. ..................... 351/208; 351/204; 351/221

(58) Field of Classification Search ......... 351/200–205, 351/208, 221, 222
See application file for complete search history.

(56) References Cited

U.S. PATENT DOCUMENTS

| | | | |
|---|---|---|---|
| 4,812,033 A | 3/1989 | Ishikawa | |
| 5,889,576 A | 3/1999 | Fujieda | ................. 351/208 |
| 5,980,042 A | 11/1999 | Hosoi | ..................... 351/212 |
| 6,217,172 B1 * | 4/2001 | Shibutani et al. | ............ 351/204 |
| 6,494,577 B2 * | 12/2002 | Iwanaga | ................... 351/208 |
| 6,685,320 B2 * | 2/2004 | Hirohara et al. | ............. 351/221 |
| 7,001,020 B2 * | 2/2006 | Yancey et al. | ............... 351/221 |
| 2002/0036749 A1 | 3/2002 | Isogai | ..................... 351/206 |

FOREIGN PATENT DOCUMENTS

EP    1 245 182 A1    10/2002
JP    9-66027         3/1997

OTHER PUBLICATIONS

EPO Communication (May 4, 2004) w/EPO Search Report (Mar. 25, 2004).

* cited by examiner

*Primary Examiner*—Jessica T Stultz
(74) *Attorney, Agent, or Firm*—Morgan & Finnegan, LLP

(57) ABSTRACT

In an ophthalmologic apparatus, the coordinates of three illuminated spots on a cornea-reflected image calculated from a front eye part image picked up by a two-dimension image pickup element and a pupil diameter are calculated, and the position of the centroid of the pupil is calculated from the front eye part image. When the pupil diameter is smaller than a predetermined value, alignment is effected from the shift from the center of the pupil, and when the pupil diameter is larger than the predetermined value, alignment is effected on the basis of the shift amounts from the illuminated spots on the cornea-reflected image. Also, a controlling method is changed over by the difference between the positions of the illuminated spots on the cornea-reflected image and the position of the centroid of the pupil. Also, the tolerance level of alignment is varied by the size of the pupil diameter.

2 Claims, 13 Drawing Sheets

OPTHALMOLOGIC APPARATUS

BACKGROUND OF THE INVENTION

1. Field of the Invention

This invention relates to an ophthalmologic apparatus for automatically effecting the alignment of an eye examining portion with an eye to be examined.

2. Description of Related Art

In a method of aligning with an eye to be examined in a conventional eye refractive power measuring apparatus for projecting a measuring beam onto the pupil of the eye to be examined, and effecting examination by reflected light from the fundus thereof, alignment is effected on the basis of the vertex of the cornea of the eye to be examined. Depending on the eye to be examined, however, there is a case where the pupil thereof and the vertex of the cornea are eccentric from each other, and when the eccentricity is great, the beam necessary for measurement is eclipsed by an iris and sometimes it becomes difficult to obtain a correct measurement value.

Also, for the accurate measurement of refractive power, it is better in accuracy to measure the refractive power at the center of the pupil which is the original visual line and therefore, there is known an apparatus as shown in Japanese Patent Application Laid-Open No. H9-66027 wherein the measurement of the refractive power is effected with a measurement optical axis aligned with the center of the pupil. In this example of the prior art, however, when the pupil of an eye to be examined is large, the eyelid becomes liable to cover the area of the pupil, and when the eyelid covers the area of the pupil, it becomes difficult to find the accurate central position of the pupil by such a simple calculation as finds the centroid of the pupil to thereby find the center of the pupil, and there is the undesirable possibility that measurement is effected at a position differing from the center of the pupil.

Also, depending on the manner in which the eyelid covers the area of the pupil, there is the problem that the detected position of the center of the pupil does not become constant, and during each measurement, the position measured changes and the measurement value is not stable. Further, there is the problem that to find the center of the pupil accurately with the eyelid covering the area of the pupil, complicated calculation becomes necessary and the calculation time becomes long and also the measurement time becomes long, and this applies an excess burden to an examinee.

Also, when the pupil of the eye to be examined is small and the diameter thereof is approximate to a measurable minimum pupil diameter, there is the possibility that even if alignment shift is within an allowable range, depending on the shift, the measuring beam is eclipsed by the iris. When the measuring beam is eclipsed by the iris, there is the problem that a measurement error will occur or a measurement value of low reliability will result.

Also, if the accuracy of alignment is made severe, much time is required of the alignment and therefore, the allowable range is set within a range which does not affect the measurement value. Usually, this allowable range of alignment is fixed, but as described in Japanese Patent 3161544, there is known an apparatus which can manually change the accuracy of alignment.

Also, in an apparatus described in Japanese Patent Application Laid-Open No. H11-19040, design is made such that measurement is effected with alignment adjusted to a position as nearest as possible to the vertex of the cornea at which the measuring beam is not eclipsed by the edge of the iris. In the above-described examples of the prior art, however, there is the problem that from the completion of the alignment till the completion of the measurement, much time is required of fog operation or the like which eliminates the adjusting power of the eye to be examined, and in the meantime, the eye to be examined moves, or when fog operation is effected, the diameter of the pupil changes, whereby even if upon completion of the alignment, the measuring beam is not eclipsed by the iris, during the actual measurement, the measuring beam covers the iris and faulty measurement occurs.

SUMMARY OF THE INVENTION

It is an object of the present invention to solve the above-noted problems and to provide an ophthalmologic apparatus which can effect alignment accurately and quickly to thereby accomplish measurement.

An ophthalmologic apparatus according to the present invention for achieving the above object is characterized by control means for calculating the central position and pupil diameter of the pupil of an eye to be examined, and when the diameter of the pupil of the eye to be examined is larger than a predetermined value, detecting the positional shift between the position of the vertex of a cornea and an eye examining portion and effecting the alignment of the eye examining portion at a proper position, and when the diameter of the pupil of the eye to be examined is smaller than the predetermined value, detecting the positional shift between the center of the pupil of the eye to be examined and the eye examining portion, and effecting the alignment of the eye examining portion at a proper position.

Also, the above-described ophthalmologic apparatus is characterized in that the pupil diameter of the pupil and the amount of eccentricity between the center of the pupil and the vertex of the cornea and a measurable minimum pupil diameter are compared with one another and when it is determined that the measuring beam is eclipsed by an iris, the positional shift between the center of the pupil and the eye examining portion is detected, and the position of the eye examining portion is adjusted to a proper position, and when it is determined that the measuring beam is not eclipsed by the iris, the positional shift between the position of the top of the cornea detected by the detecting means and the eye examining portion is detected, and the position of the eye examining portion is adjusted to the proper position.

Also, an ophthalmologic apparatus for detecting the positional shift between the center of the pupil and an eye examining portion and effecting the alignment of the eye examining portion at a proper position is characterized in that the tolerance level of the alignment between the eye examining portion and an eye to be examined is changed in conformity with the size of the diameter of the pupil of the eye to be examined.

Further objects and constructions of the present invention will become apparent from the following description of some embodiments of the present invention.

DETAILED DESCRIPTION OF THE PREFERRED EMBODIMENTS

First Embodiment

A first embodiment of the present invention will hereinafter be described in detail.

Figure 1:
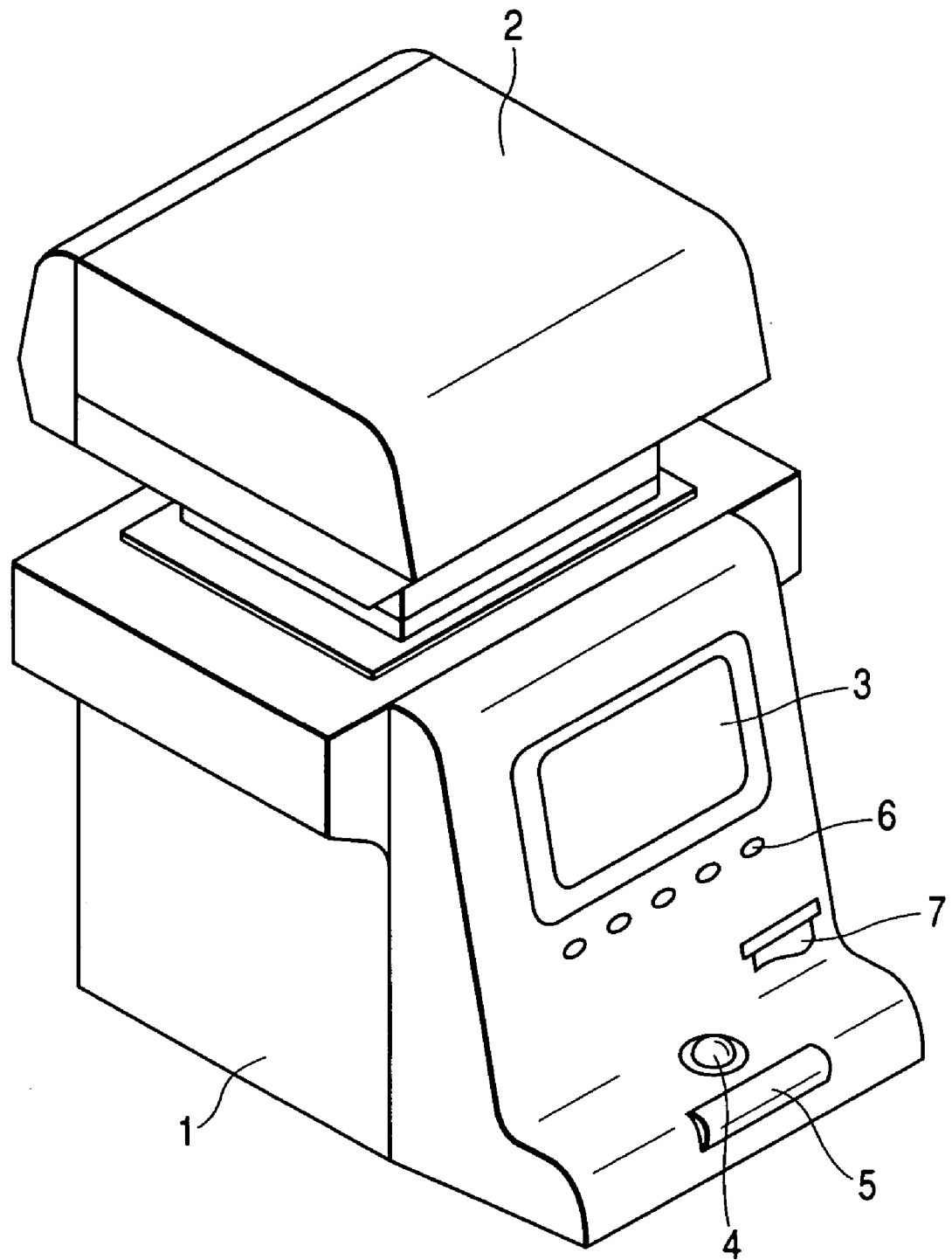
FIG. 1 is a pictorial perspective view of an eye refraction measuring apparatus

Referring to FIG. 1 which is a pictorial perspective view of an eye refraction measuring apparatus, an eye examining portion 2 is movably placed on the upper portion of a base stand 1, and on the operation surface of the base stand 1, there are disposed a display portion 3 comprising a liquid crystal monitor and a CRT monitor or the like for selecting the display of a measurement value, the image of an eye to be examined, etc. and the setting of various devices, a track ball 4 for operating the display screen surface thereof, and roughly aligning the eye examining portion 2 with the eye to be examined, a roller 5, a switch panel 6 on which a printer printing switch, a measurement starting switch, a selection setting switch, etc. are disposed, and a printer 7 for printing the result of measurement. An examinee places his or her face on a face receiving portion, not shown, which is disposed on a side opposite to the operation surface of the base stand 1, and places his or her eye to be examined in front of the objective part of the eye examining portion 2, whereby measurement becomes possible.

Figure 2:
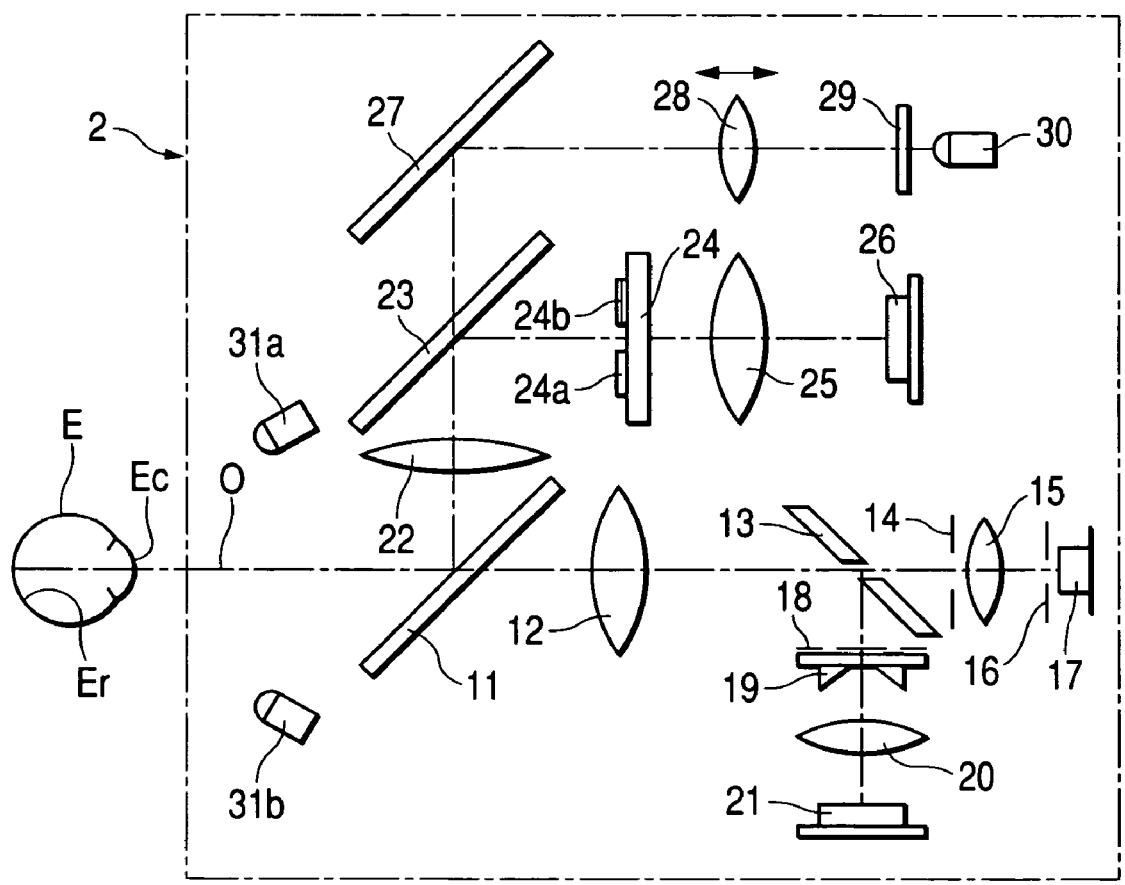
FIG. 2 shows the optical construction of an eye examining portion.
Figure 3:
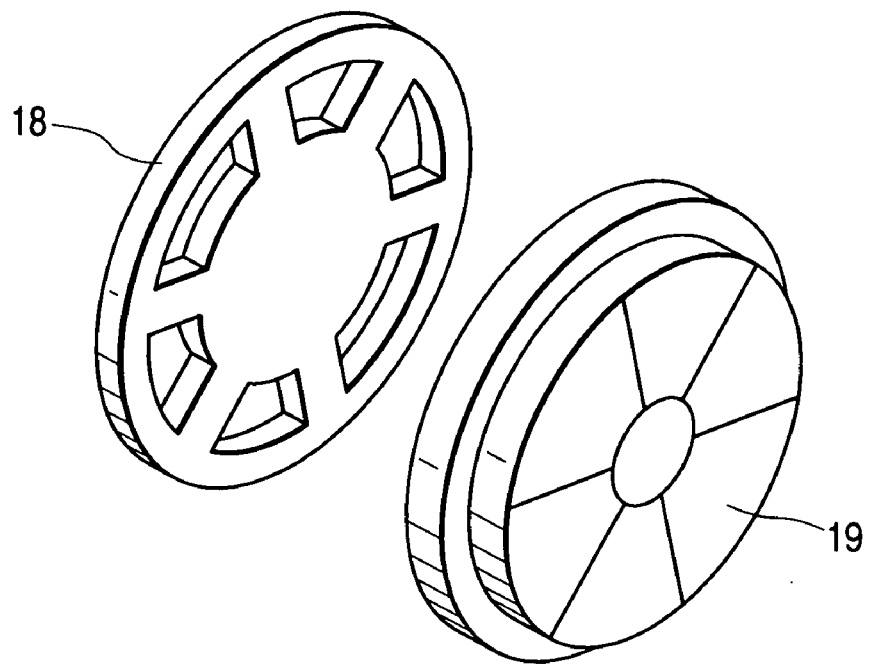
FIG. 3 is a perspective view of a six-division stop and a six-division prism.

Referring now to FIG. 2 which shows the optical construction of the interior of the eye examining portion 2, on the optical axis O of the eye examining portion 2 which is to be aligned with the visual line of the eye E to be examined, there are arranged, in succession from the eye E to be examined side, a dichroic mirror 11 for totally reflecting visible light and partly reflecting a beam of a wavelength 880 nm, an objective lens 12, an apertured mirror 13, a stop 14, a projection lens 15, a projection stop 16 and a measurement light source 17 emitting the beam of wavelength 880 nm. In the direction of reflection of the apertured mirror 13, there are disposed in succession a six-division stop 18, a six-division prism 19, a light receiving lens 20 and a two-dimension image pickup element 21. The six-division stop 18 and the six-division prism 19 are of such shapes as shown in FIG. 3, and actually the six-division stop 18 and the six-division prism 19 are brought into close contact with each other.

Figure 4:
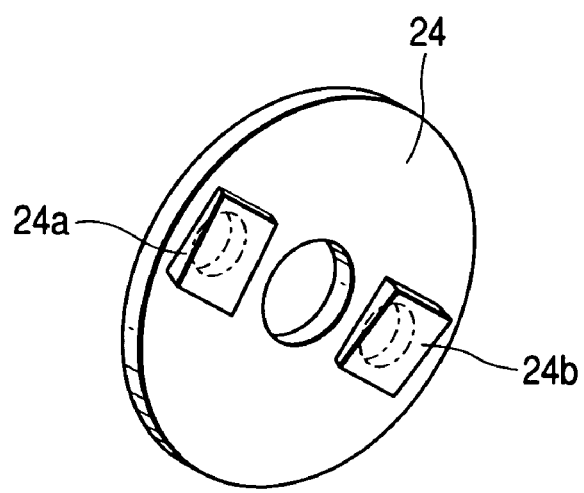
FIG. 4 is a perspective view of an alignment prism stop.

On the other hand, in the reflecting direction of the dichroic mirror 11, there are disposed a fixation target projection optical system and a light receiving optical system used in common for front eye part observation and alignment detection. As the light receiving optical system, there are arranged in succession a lens 22, a dichroic mirror 23, an alignment prism stop 24, an imaging lens 25 and a two-dimension image pickup element 26. The alignment prism stop 24 is of such a shape as shown in FIG. 4, wherein three opening portions are provided in a row in a disc-shaped stop plate, and alignment prisms 24a and 24b transmitting therethrough only a beam of a wavelength in the vicinity of 880 nm are adhesively secured to that side of the opening portions on both sides which is adjacent to the dichroic mirror 23.

As the fixation target projection optical system, a total reflection mirror 27, a fixation guide lens 28, a fixation chart 29 and a fixation target light source 30 are arranged in succession on the transmission side of the dichroic mirror 23. On both sides of the optical axis O forward of the eye E to be examined, there are provided external eye illumination sources 31a and 31b.

Figure 5:
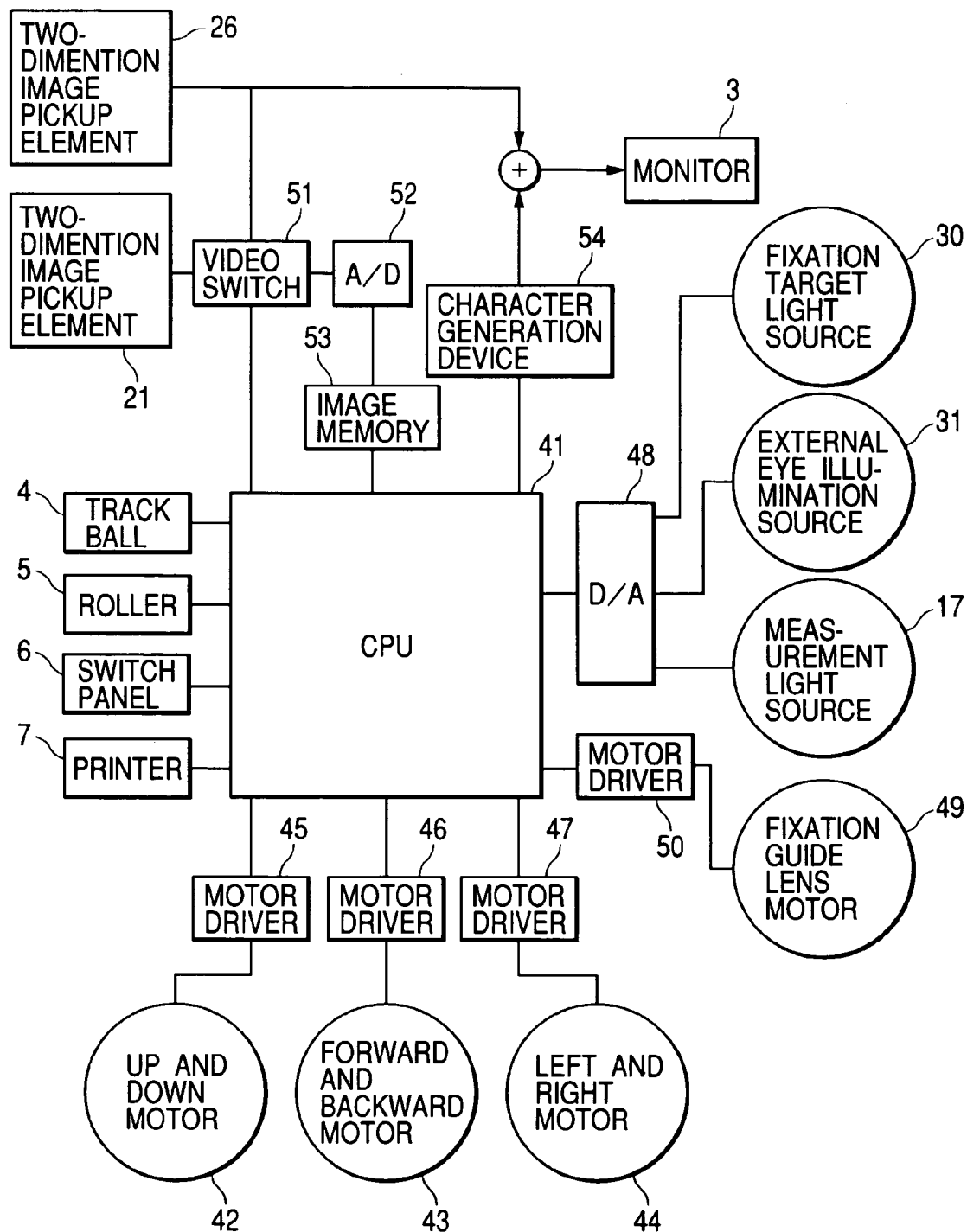
FIG. 5 is a block circuit diagram.

Referring to FIG. 5 which shows a block circuit diagram of the eye refraction measuring apparatus, the track ball 4, the roller 5, the switch panel 6 and the printer 7 are connected to a CPU 41 for effecting control, calculation, etc. Also, an up and down motor 42, a forward and backward motor 43 and a left and right motor 44 for driving the eye examining portion 2 are connected to the CPU 41 through motor drivers 45, 46 and 47, respectively. The fixation target light source 30, the external eye illumination source 31 and the measurement light source 17 are further connected to the CPU 41 through a D/A converter 48, and a fixation guide lens motor 49 for driving the fixation guide lens 28 is connected to the CPU 41 through a motor driver 50.

The outputs of the two-dimension image pickup elements 21 and 26 are connected to a video switch 51, and are capable of switching over to be transmitted to an A/D converter 52 in accordance with a signal from the CPU 41. An image data converted by the A/D converter 52 is stored into an image memory 53. The image memory 53 is connected to the CPU 41 which is capable of accessing the image data stored within the image memory 53. Also, the output of the two-dimension image pickup element 21 is combined with a signal from the CPU 41 through a character generation device 54, and is connected to the display portion 3.

In the thus constructed eye refraction measuring apparatus, an operator first puts the examinee's face on the face receiving stand, and thereafter operates the track ball 4 and the roller 5 to adjust the optical axis O of the eye examining portion 2 to the eye E to be examined. The operation of the track ball 4 can be accomplished by moving the eye examining portion 2 leftwardly and rightwardly and forwardly and backwardly relative to the eye E to be examined, and the roller. 5 can be aligned by moving the eye examining portion 2 upwardly and downwardly.

In this operation, on the apparatus side, output signals from a pulse counter and a rotary encoder contained in the track ball 4 and the roller 5, respectively, can be received by the CPU 41 to thereby detect an operation amount and a speed. Further, from the operation amount and the speed, the up and down motor 42, the forward and backward motor 43 and the left and right motor 44 are driven through the respective motor drivers 45, 46 and 47.

During fixation guide, the projection beam of the fixation target light source 30 turned on illuminates the fixation chart 29 from the back side thereof, and is projected onto the fundus Er of the eye E to be examined through the fixation guide lens 28 and the lens 22. The fixation guide lens 28 is moved in the direction of the optical axis thereof by the rotation of the fixation guide lens motor 49 so as to be capable of coping with a change in the visibility of the eye E to be examined.

A light source for alignment detection is used in common with the measurement light source 17, and a beam from the measurement light source 17 is reflected by the cornea Ec of the eye E to be examined, and the cornea-reflected beam is reflected by the dichroic mirror 11, passes through the lens 22, is reflected by the dichroic mirror 23 and is directed to the alignment optical system. In the alignment optical system, the beam transmitted through the alignment prism 24a of the alignment prism stop 24 is downwardly refracted, and the beam transmitted through the alignment prism 24b is upwardly refracted. Also, the beam passing through the central opening portion is intactly transmitted, and three illuminated spots are imaged on the two-dimension image pickup element 26 through the imaging lens 25.

The front eye part image of the eye E to be examined and the cornea-reflected image by the external eye illumination sources 31a and 31b of wavelength 880 nm are also reflected by the dichroic mirror 11, pass through the lens 22, are further reflected by the dichroic mirror 23, are directed to the alignment optical system, pass through only the central opening portion of the alignment prism stop 24, and are imaged on the two-dimension image pickup element 26 through the imaging lens 25.

The video signal of the front eye part image picked up by the two-dimension image pickup element 26 is converted into digital data by the A/D converter 52 through the video switch 51, and is stored in the image memory 53. The CPU 41 carries out image processing such as the extraction of an alignment illuminated spot and the extraction of the pupil on the basis of the image stored in the image memory 53. Also, the video signal of the front eye part image picked up by the two-dimension image pickup element 26 is combined with a signal from the character generation device 54, and displays the front eye part image, the measurement value, etc. on the display portion 3. Also, as required, the measurement value, etc. are printed on the printer 7.

Figure 6A:
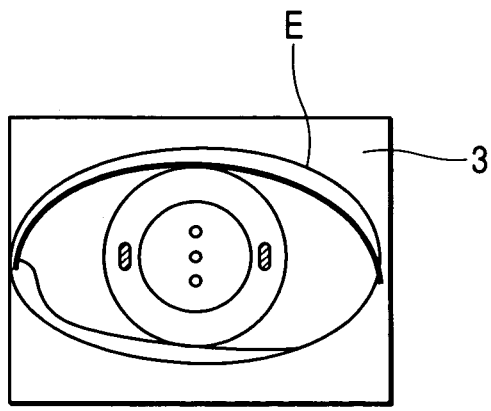
FIGS. 6A, 6B and 6C are illustrations of front eye part images corresponding to alignment states.
Figure 6B:
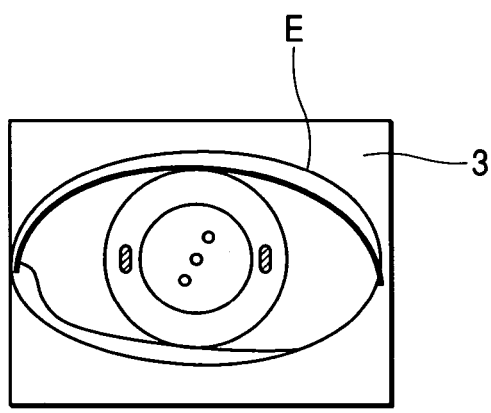
Figure 6C:
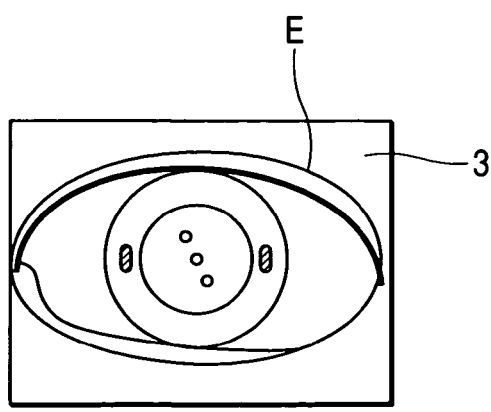

FIGS. 6A to 6C are illustrations of the screen surface of the display portion 3, and show the front eye part image of the eye E to be examined picked up by the two-dimension image pickup element 26. The front eye part image of the eye E to be examined and the cornea-reflected image of the external eye illumination sources 31a, 31b are formed on the left and right of the pupil image by the beam transmitted through the central opening portion of the alignment prism stop 24. Also, the cornea-reflected image by the measurement light source 17 is formed as three illuminated spots in a column. That is, the beam transmitted through the alignment prism 24a of the alignment prism stop 24 becomes an upper illuminated spot, the beam transmitted through the alignment prism 24b becomes a lower illuminated spot, and the beam transmitted through the central opening portion becomes a central illuminated spot.

FIG. 6A shows a state in which the working distance of the eye E to be examined has been properly aligned, FIG. 6B shows the front eye part image in a state in which the working distance between the eye E to be examined and the eye examining portion 2 is farther than a proper position, and FIG. 6C shows the front eye part image in a state in which the working distance between the eye E to be examined and the eye examining portion 2 is nearer than the proper position. The alignment shift in the direction of the working distance of alignment is calculated from the shift of the upper and lower illuminated spots in the X coordinates, and the alignment shift in the up and down and left and right directions is calculated from the position of the central illuminated spot.

The operator moves the eye examining portion 2 by the above-described operation, carries out some degree of alignment so that the three illuminated spots by the cornea-reflected light of the alignment light can be seen on the cornea Ec of the eye E to be examined through the display portion 3, and-when the three illuminated spots are confirmed on the display portion 3, the operator depresses the measurement starting switch disposed on the switch panel 6 to thereby start automatic alignment.

Figure 7:
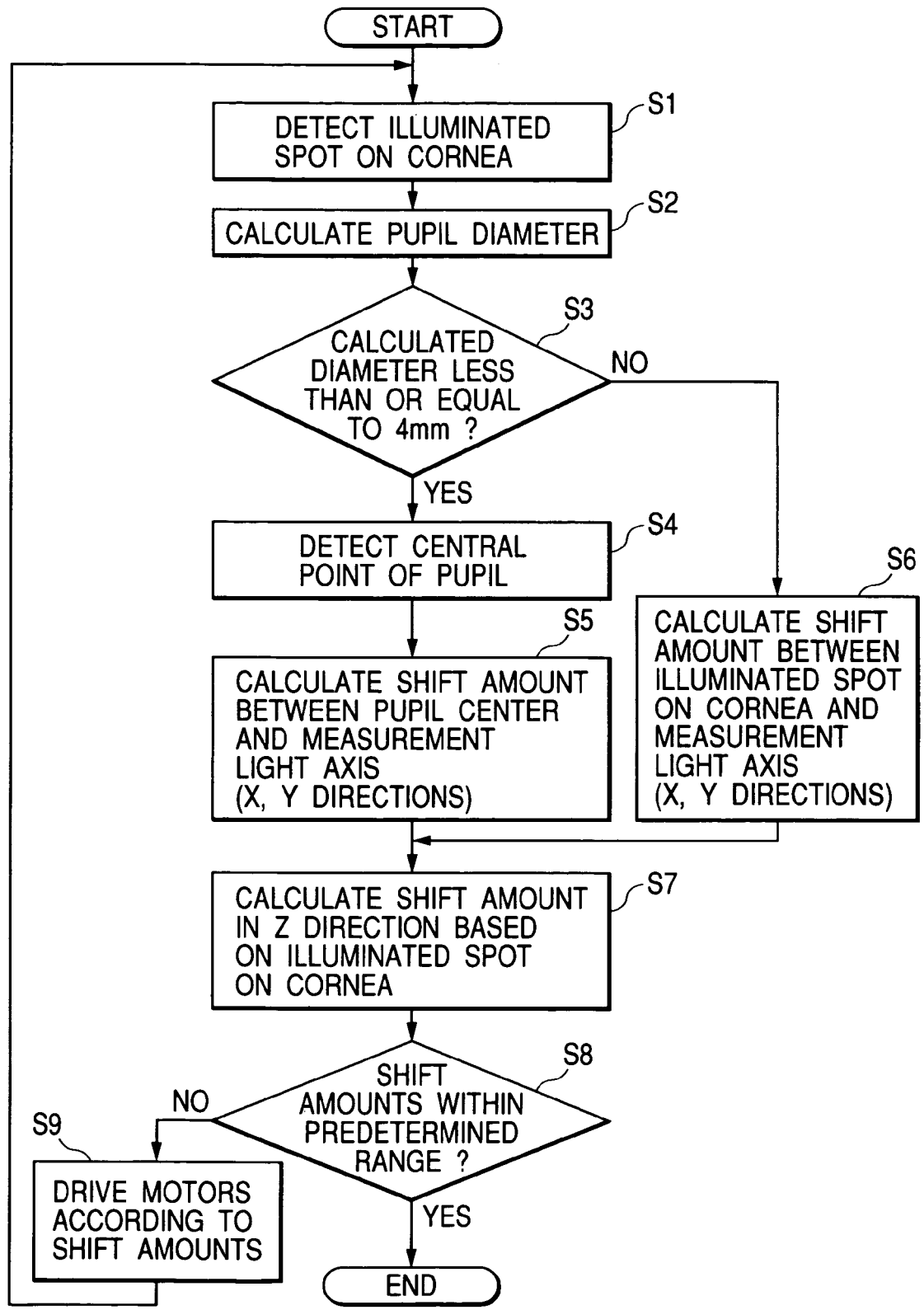
FIG. 7 is a flow chart of the automatic alignment of a first embodiment.

FIG. 7 shows a flow chart of the automatic alignment, and first at a step S1, the video signal of the front eye part image of the eye E to be examined picked up by the two-dimension image pickup element 26 is converted into digital data through the A/D converter 52 and is introduced into the image memory 53, and the three illuminated spots on the cornea-reflected image by the measurement light source 17 are extracted from the front eye part image in the image memory 53 by the CPU 41, and the coordinates of each illuminated spot are detected.

Figure 8:
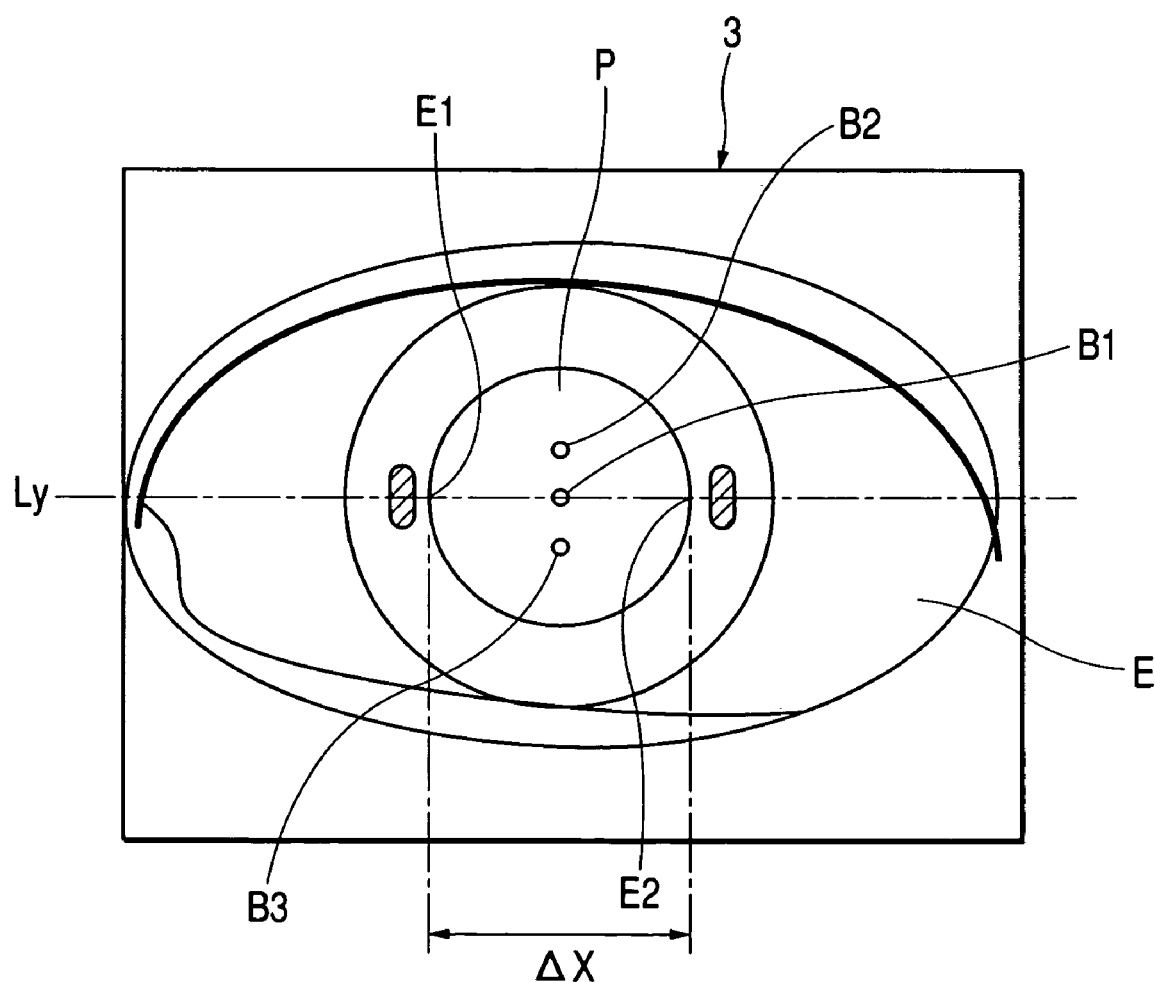
FIG. 8 is an illustration showing the manner in which the diameter of a pupil is found.

FIG. 8 shows the front eye part image of the eye E to be examined introduced into the image memory 53, and at a step S2, the edges E1 and E2 of the pupil P and the iris, respectively, are detected on a line Ly in a horizontal direction on the Y coordinates of the central illuminated spot B1 of the three illuminated spots on the cornea-reflected image. detected at the step S1, and the distance $\Delta X$ between the edges E1 and E2 is calculated, and the pupil diameter of the pupil P of the eye E to be examined is found from this distance $\Delta X$.

Next, shift is made to a step S3, where the size of the pupil diameter of the pupil P calculated at the step S2 is judged, and if the pupil diameter is, for example, less than or equal to 4 mm, shift is made to a step S4, and if the pupil diameter is larger than 4 mm, shift is made to a step S6.

At the step S4, the centroid position of the pupil P is calculated from the front eye part image of the eye E to be examined introduced into the image memory 55 to thereby find the center of the pupil. Subsequently, at a step S5, the shift amount of alignment between the center of the pupil and the measurement light axis of the apparatus in the left and right and up and down X, Y direction is calculated, and shift is made to a step S7.

If at the step S3, the pupil diameter is judged to be larger than 4 mm, at the step S6, the shift amounts of alignment in X, Y directions with the measurement light axis of the apparatus are calculated from the coordinates of the central illuminated spot B1 of the three illuminated spots on the cornea-reflected image detected at the step S1, and shift is made to the step S7. At the step S7, the shift amount of alignment in Z direction which is the working distance is found from the shift of the X coordinates of the upper and lower illuminated spots B2 and B3 on the cornea-reflected image detected at the step S1.

At a step S8, whether the shift amounts in X, Y and Z directions are within a predetermined range is determined, and if the shift amounts are greater than the predetermined range, shift is made to a step S9, where the up and down motor 42, the forward and backward motor 43 and the left and right motor 44 are driven according to the shift amounts to thereby make the shift of alignment small, and return is made to the step S1.

The above-described steps are repeated until at the step S8, the shift amounts are judges to be within the predetermined range, and after the completion of the automatic alignment operation, a measuring operation is performed to thereby calculate a measurement value.

Figure 9A:
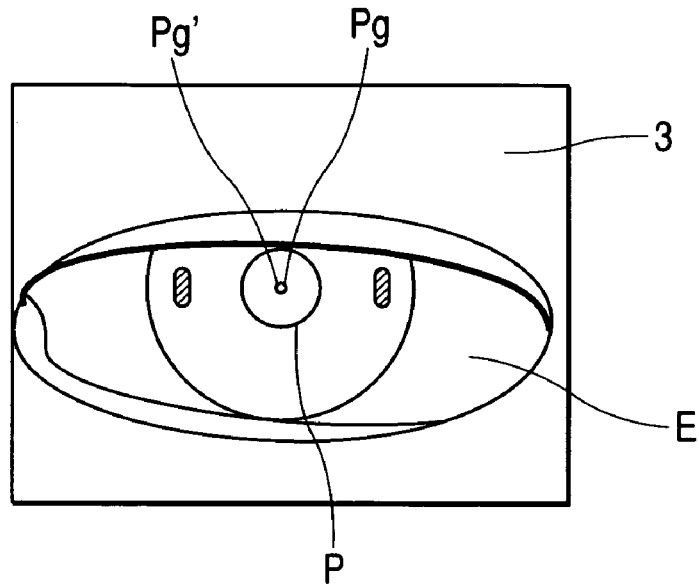
FIGS. 9A and 9B are illustrations of the front eye part image in a state in which the eyelid hangs down.
Figure 9B:
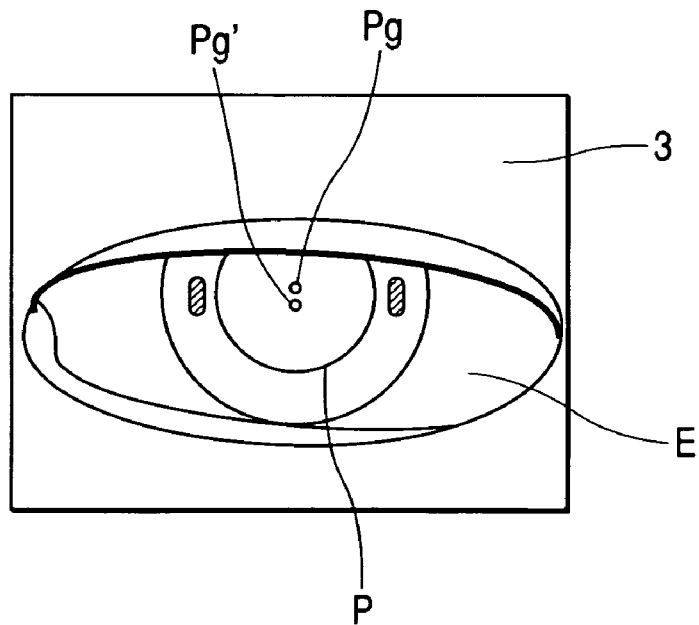

Description will now be made of the reason for changing over the alignment detecting method in X, Y directions depending on the pupil diameter at the step S3. FIG. 9A shows the front eye part image in a state in which the pupil diameter of the eye E to be examined is small and the eyelid hangs down, and FIG. 9B shows the front eye part image in a state in which the pupil diameter of the eye E to be examined is large and the eyelid hangs down. When as shown in FIG. 9A, the pupil diameter is small, even if the eyelid hangs down a little, the eyelid does not cover the pupil area and therefore, the original center Pg of the pupil and the calculated center Pg' of the pupil P substantially coincide with each other.

When, however, as shown in FIG. 9B, the pupil diameter is large, if the eyelid hangs down only a little, the eyelid covers the pupil area. When the centroid of the pupil P is found in such a state, the calculated center Pg' of the pupil shifts from the original center Pg of the pupil.

Also, this shift is varied by the amount by which the eyelid covers the pupil area and therefore cannot be measured at a stable position. Accordingly, even if the same eye E to be examined is measured, when the pupil P is large, the measuring position becomes uneven during each measurement, and this leads to the undesirable possibility that it will become difficult to obtain a stable measurement value.

In the measurement after alignment has been finished, the beam emitted from the measurement light source 17 is stopped down by the projection stop 16, is primary-images on this side of the objective lens 12 by the projection lens 15, enters the center of the pupil of the eye E to be examined through the objective lens 12 and the dichroic mirror 11, and is imaged on the fundus Er of the eye. The reflected light from the fundus Er of the eye passes through the periphery of the pupil and again enters the objective lens 12, and becomes a thick beam and is totally reflected by the apertured mirror 13. The beam reflected on the apertured mirror 13 is divided into six by the six-division stop 18 and also, is refracted by the six-division prism 19 so as to be received within the proper range of the light receiving surface area of the two-dimension image pickup element 21, and six spot images are projected onto the two-dimension image pickup element 21.

The video signal of the eye fundus image picked up by the two-dimension image pickup element 21 is converted into digital data by the A/D converter 52 through the video switch 51, and is stored in the image memory 53. The CPU 41 effects the calculation of the eye refractive power on the basis of the positions of the spot images of the image stored in the image memory 53.

Originally, the refractive power is measured at the center of the pupil, but when the pupil is large, even if measurement is effected with alignment adjusted to the vertex of the cornea even when the vertex of the cornea and the pupil are eccentric from each other, the measuring beam is little eclipsed by the iris. Also, there is the desirable possibility that an error occurs between the measurement value at the center of the cornea and the measurement value at the center of the pupil, but it is possible to solve the problem that the eyelid covers the pupil area, whereby the measuring position on the pupil is changed and the measurement value becomes unstable.

As described above, by using the ophthalmologic apparatus of the present invention, even if the eyelid covers the pupil area in a case that the pupil of the eye to be examined is large, it is possible to effect the alignment and measurement with high speed.

Second Embodiment

A second embodiment will now be described with reference to FIGS. 10 to 12.

The ophthalmologic apparatus main body of FIGS. 1 to 6 described in the first embodiment need not be described.

Figure 10:
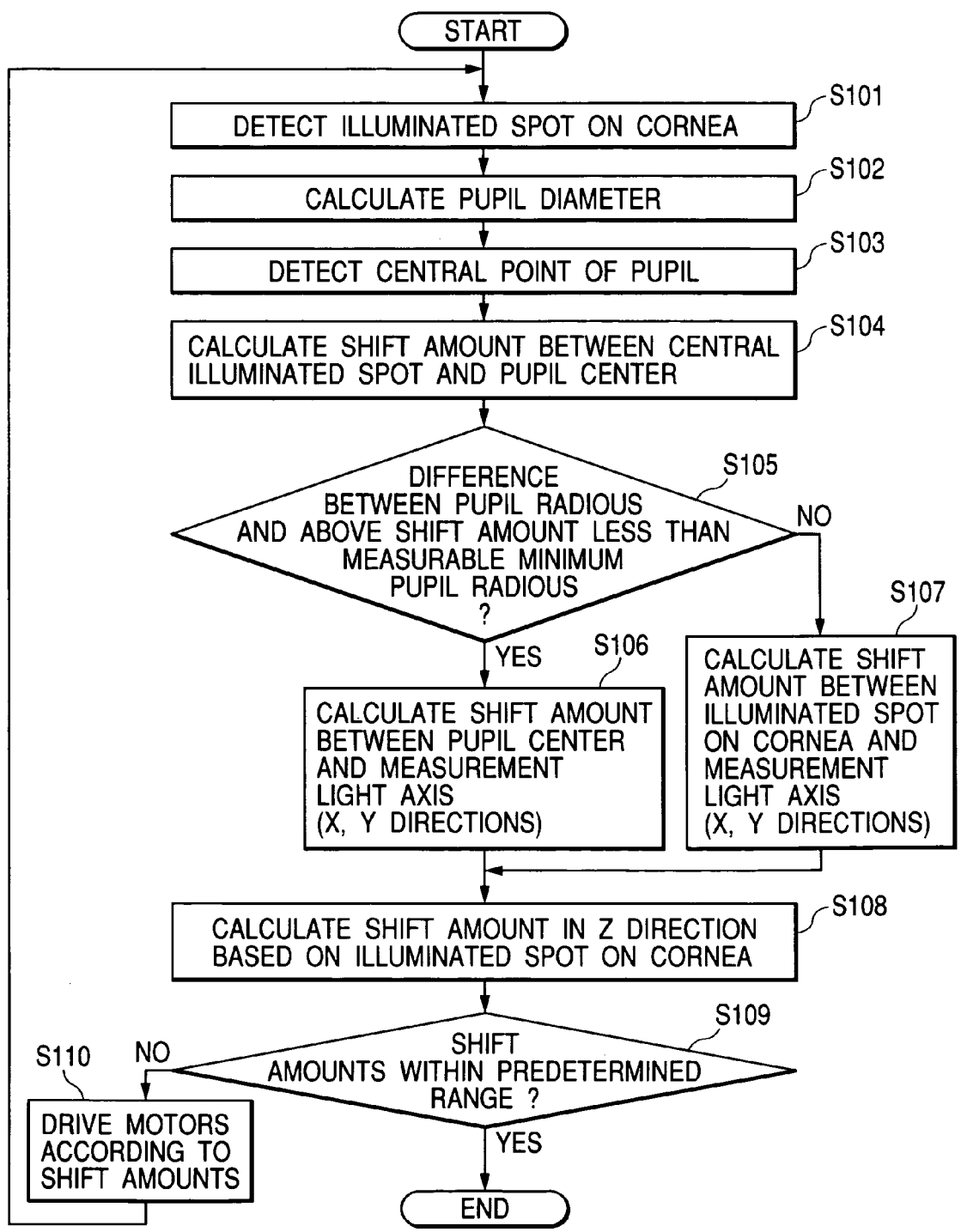
FIG. 10 is a flow chart of the automatic alignment of a second embodiment.
Figure 11:
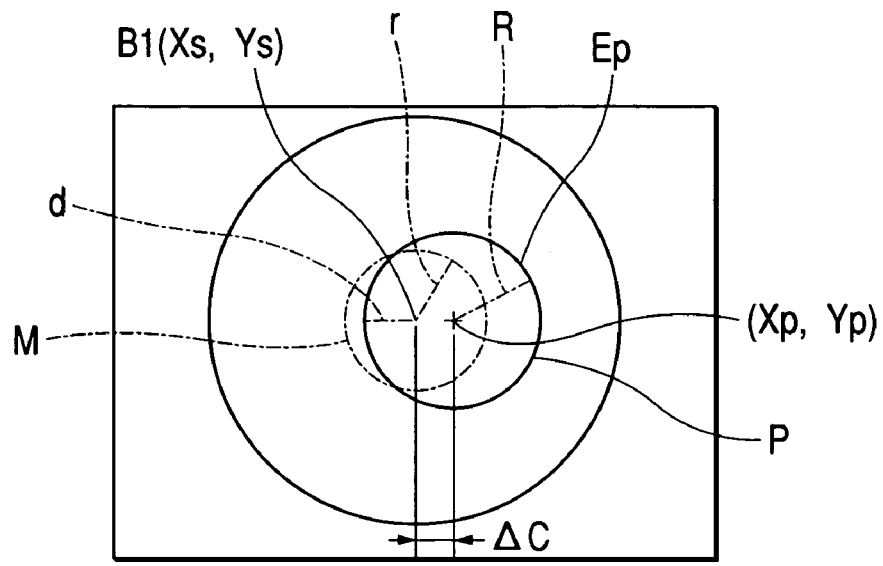
FIG. 11 is an illustration of a pupil, the vertex of a cornea and a measuring beam.

Referring to FIG. 10 which shows a flow chart of automatic alignment, first at a step S101, the video signal of the front eye part image of the eye E to be examined picked up by the two-dimension image pickup element 26 is converted into digital data through the A/D converter 52 and is introduced into the image memory 53, and three illuminated spots on the cornea-reflected image by the measurement light source 17 are extracted from the front eye part image in the image memory 53 by the CPU 41, and the coordinates of each illuminated spot are detected. At a step S102, the area of the pupil is calculated from the front eye part image introduced into the image memory 53 at the step S101, and assuming that the pupil is circular, the radius of the pupil is calculated. Subsequently, at a step S103, the centroid of the pupil is found to thereby detect the coordinates of the central position of the pupil Further, at a step S104, as shown in FIG. 11, from the coordinates (Xs,Ys) of the central illuminated spot B1 of-the three illuminated spots detected at the step S101 and the coordinates (Xp,Yp) of the center of the pupil Ep detected at the step S103, the calculation of $(|Xs-Xp|^2+|Ys-Yp|^2)^{1/2}$ is effected to thereby calculate the amount of eccentricity ΔC between the central illuminated spot B1 and the center of the pupil.

Next, shift is made to a step S105, where the shortest distance from the position of the vertex of the cornea to the edge of the pupil is calculated. When the radius of the pupil is defined as R and the amount of eccentricity between the pupil Ep and the vertex of the cornea is defined as ΔC, the shortest distance d from the position of the vertex of the cornea to the edge of the pupil can be calculated by (pupil radius R—amount of eccentricity ΔC). That is, when the value of this shortest distance d is equal to or less than the measurable minimum pupil radius r, as shown in FIG. 11, the measuring beam M is outside the boundary line P between the pupil Ep and the iris and therefore, it is eclipsed by the iris and thus, shift is made to a step S106. Also, if (pupil radius R-amount of eccentricity ΔC) is greater than the measurable minimum pupil radius r, the measuring beam is not eclipsed by the iris and thus, shift is made to a step S107.

While in the present embodiment, the shortest distance d from the position of the vertex of the cornea to the edge of the pupil and the measurable minimum pupil radius have been compared with each other, the shortest distance d may be compared with a value a little greater than the measurable minimum pupil radius r with a surplus.

At the step S106, the shift amounts of alignment with the measurement light axis of the eye examining portion 2 in X, Y directions which are left and right and up and down directions are calculated from the coordinates of the center of the pupil calculated at the step S103, and shift is made to a step S108.

Also, at the step S107, the shift amounts of alignment with the measurement light axis of the eye examining portion 2 in X, Y directions are calculated from the coordinates of the central illuminated spot B1 of the three illuminated spots on the cornea-reflected image detected-at the step S101, and shift is made to the step S108.

Subsequently, at the step S108, the shift amount of alignment in Z direction which is the working distance direction is calculated from the shift amount of the X coordinates of the upper and lower illuminated spots on the cornea-reflected image detected at the step S101. At a step S109, whether the shift amounts in X, Y and Z directions are within a predetermined range is determined, and if the shift amounts are greater than the predetermined range, shift is made to a step S101, where the up and down motor 42, the forward and backward motor 43 and the left and right motor 44 are driven according to the shift amounts to thereby make the shift of alignment small, and return is made to the step S101.

The above-described steps S101 to S110 are repeated until at the step S109, the shift amounts are judged to be within the predetermined range, and after the completion of the automatic alignment operation, a measuring operation is performed to thereby calculate a measurement value.

In the measurement after the alignment has been completed, the beam emitted from the measurement light source 17 is stopped down by the projection step 16, is primary-imaged on this side of the objective lens 12 by the projection lens 15, enters the center of the pupil of the eye E to be examined through the objective lens 12 and the dichroic mirror 11, and is imaged-on the fundus Er of the eye. The reflected light from the fundus Er of the eye passes through the periphery of the pupil and again enters the objective lens 12, and becomes a thick beam and is totally reflected by the apertured mirror 13. The beam reflected on the apertured mirror 13 is divided into six by the six-division stop 18 and also, is refracted by the six-division prism 19 so as to be received within the proper range of the light receiving surface area of the two-dimension image pickup element 21, and six spot images are projected onto the two-dimension image pickup element 21.

The video signal of the eye fundus image picked up by the two-dimension image pickup element 21 is converted into digital data by the A/D converter 52 through the video switch 51, and is stored in the image memory 53. The CPU 41 effects the calculation of the eye refractive power on the basis of the positions of the spot images of the image stored in the image memory 53.

Figure 12:
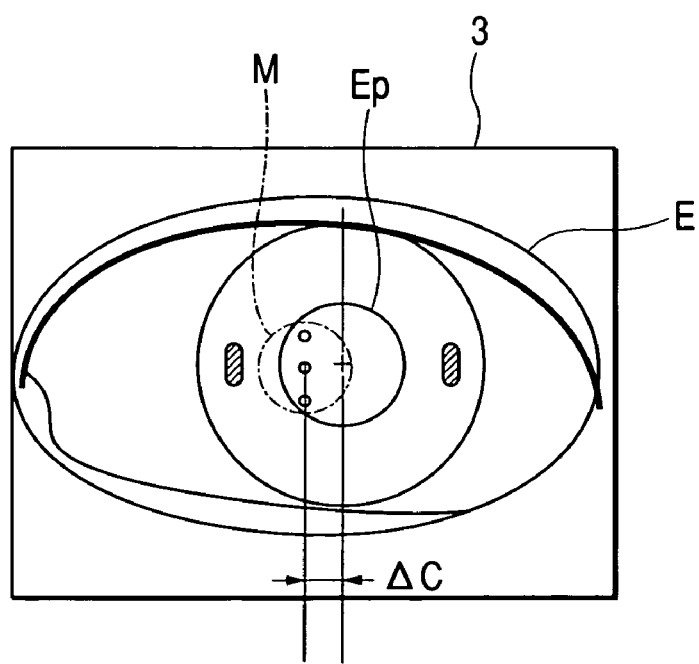
FIG. 12 is an illustration of a front eye part when the visual line shifts.

While in the present embodiment, the magnitude of the amount of eccentricity between the vertex of the cornea and the pupil Ep is not taken up as a problem, as the cause of the eccentricity between the vertex of the cornea and the pupil Ep, there are a case where the pupil Ep of the eye E to be examined is truly eccentric, and a case as shown in FIG. 12 wherein the gaze of the eye E to be examined deviates from the optical axis of the measuring beam M. Particularly, when the amount of eccentricity is great, it is often the case that the gaze deviates greatly, and in such a state, accurate measurement cannot be effected and therefore, when the amount of eccentricity ΔC is great, e.g. 2 mm or greater, it is displayed as warning on the display portion 3 that the amount of eccentricity between the vertex of the cornea and the pupil Ep is great. Alternatively, a warning mark may be printed on the printer 7 together with the measurement value to thereby inform the examiner.

Third Embodiment

A third embodiment will now be described with reference to FIGS. 13 to 15.

Figure 13:
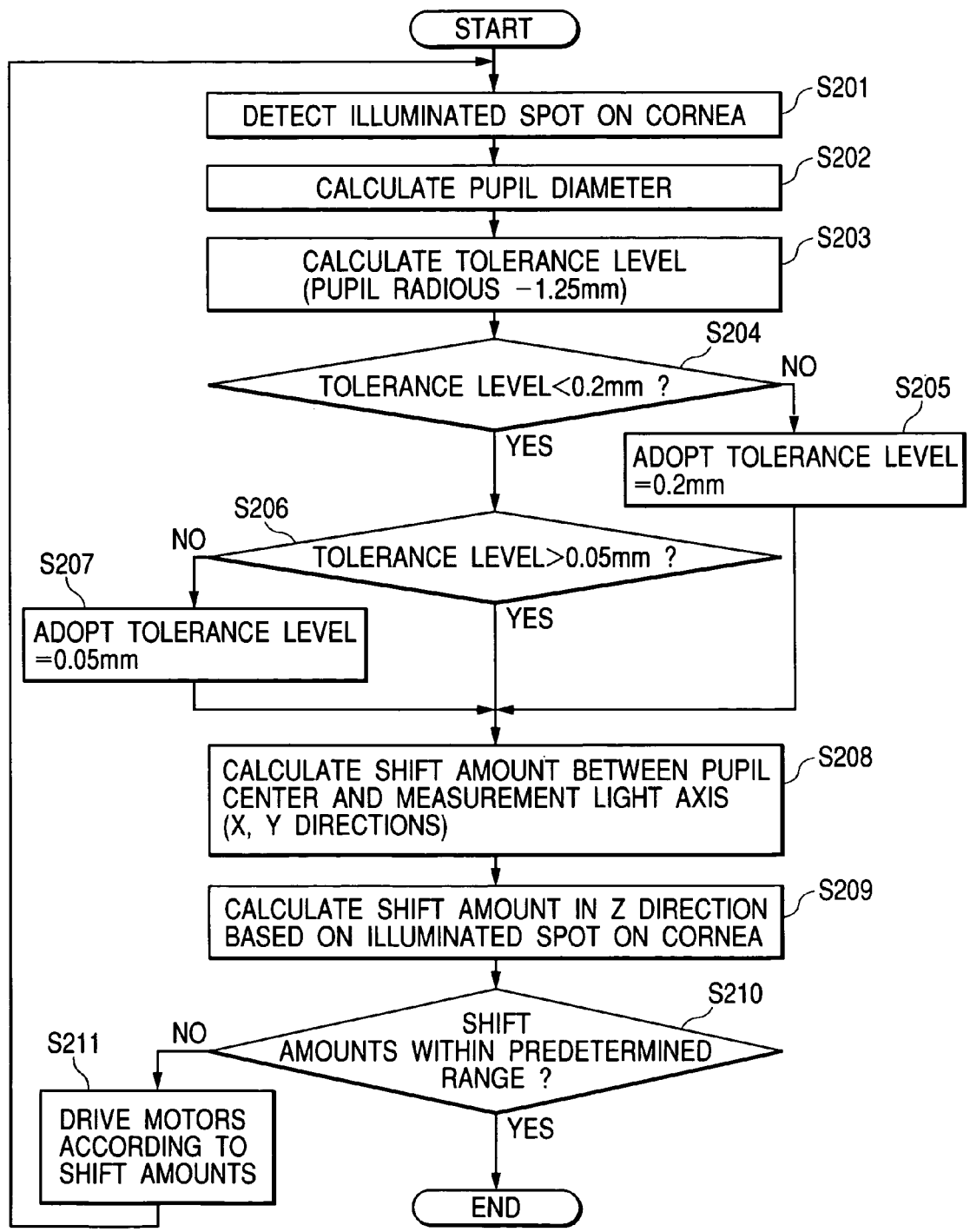
FIG. 13 is a flow chart of the automatic alignment of a third embodiment.

Referring to FIG. 13 which shows a flow chart of automatic alignment, first at a step S201, the video signal of the front eye part image of the eye E to be examined picked up by the two-dimension image pickup element 26 is converted into digital data through the A/D converter 52, and is introduced into the image memory 53, and three illuminated spots on the cornea-reflected image by the measurement light source 17 are extracted from the front eye part image in the image memory 53 by the CPU 41 to thereby detect the coordinates of each illuminated spots. Next, shift is made to a step S202, where the area of the pupil is calculated from the front eye part image introduced into the image memory 53 at the step S201, and the radius of the pupil is calculated from the calculated area.

Figure 14A:
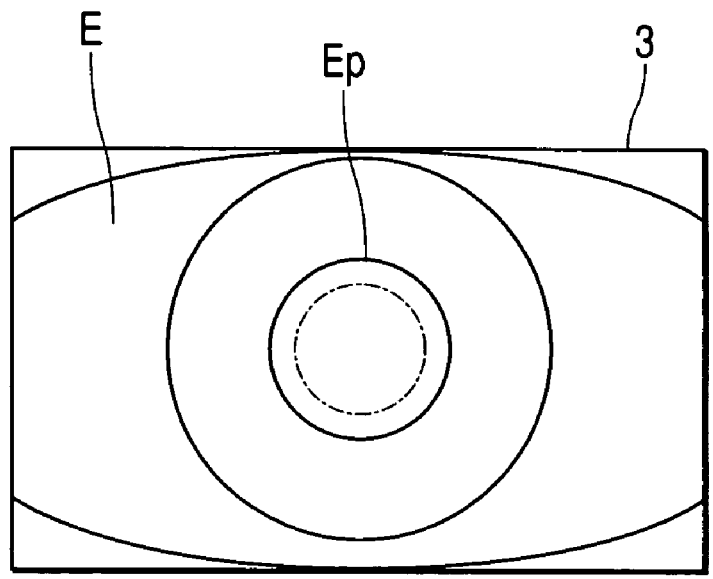
FIGS. 14A and 14B are illustrations of the front eye part image when the pupil diameter is large.
Figure 14B:
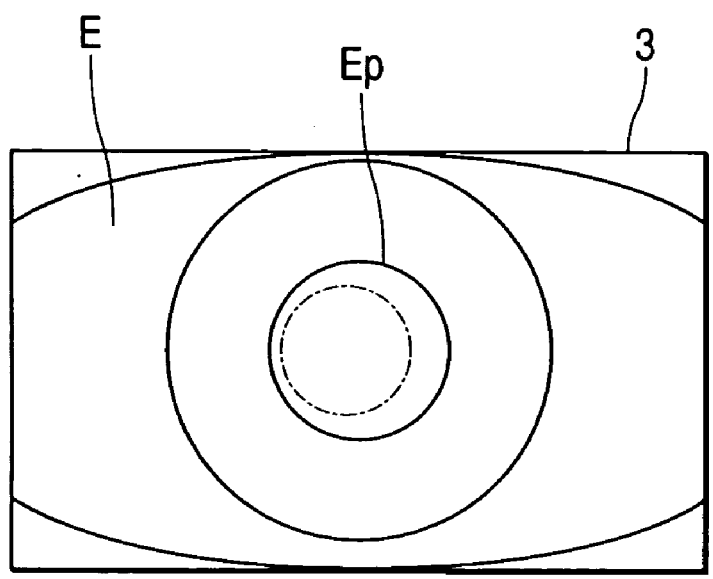

FIGS. 14A and 14B show the front eye part image of the eye E to be examined when the radius of the pupil Ep introduced into the image memory 53 is 1.5 mm, FIG. 14A shows a state in which the shift of alignment is substantially null, and FIG. 14B shows a state in which the shift of alignment is 0.2 mm which is a maximum value within a tolerance level. Usually, the tolerance level of this shift amount is 0.2 mm. A measurable minimum pupil radius is 1.25 mm. In this case, (pupil radius−measurable minimum pupil radius) is (1.5−1.25)=0.25 mm, and this is greater than 0.2 mm which is the tolerance level of the shift amount and therefore, even if the alignment shifts at maximum within the tolerance level, the measuring beam is not eclipsed by the iris.

Figure 15A:
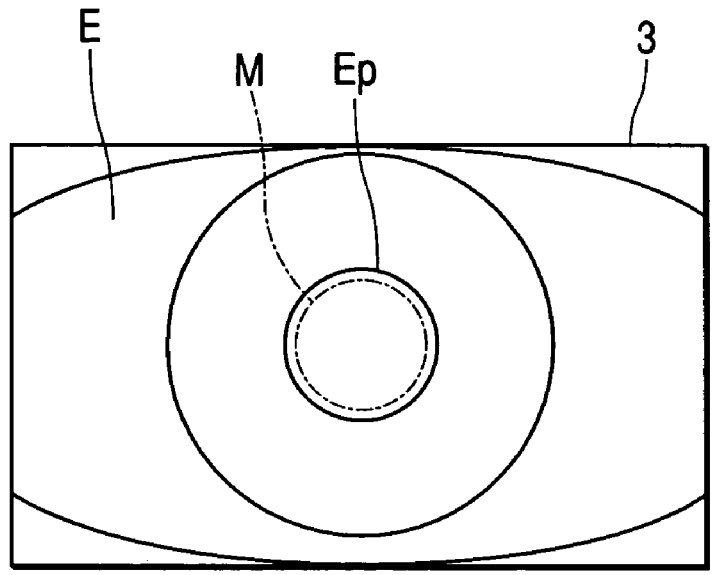
FIGS. 15A and 15B are illustrations of the, front eye part image when the pupil diameter is small.
Figure 15B:
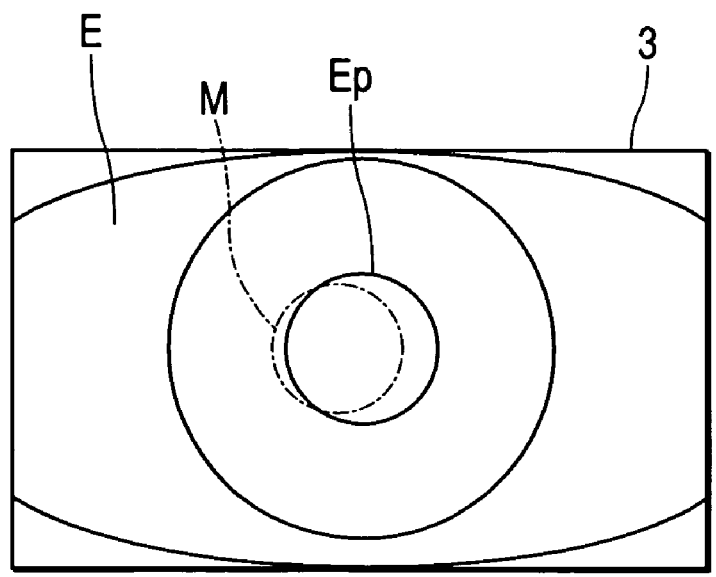

FIGS. 15A and 15B show the front eye part image of the eye E to be examined when the radius of the pupil is 1.4 mm, FIG. 15A shows a state in which the shift of alignment is substantially null, and FIG. 15B shows a state in which the alignment shifts at maximum within the tolerance level. The allowed shift amount is (1.4−1.25)=0.15 mm, and the tolerance level 0.2 mm of the shift amount of alignment is greater and therefore, as shown in FIG. 15B, there is the possibility that the measuring beam M is eclipsed by the iris. To avoid this problem, the allowed shift amount of alignment must be made equal to or less than 0.15 mm.

Therefore, at a step S203, the tolerance level of the shift amount of alignment is calculated by the calculation of (pupil radius−measurable minimum pupil radius), and shift is made to a step S204. At the step S204, the calculated tolerance level is compared with the upper limit value 0.2 mm of the tolerance level, and if it is equal to or greater than the upper limit value, at a step S205, the upper limit value 0.2 mm of the tolerance value is adopted.

If at the step S204, the calculated tolerance value is less than the upper limit value, at a step S206, it is compared with the lower limit value 0.05 mm. If it is equal to or less than the lower limit value, at a step S207, the lower limit value 0.05 mm is adopted.

When the setting of this tolerance level is completed, shift is made to a step S208, where the position of the centroid of the pupil Ep is calculated from the front eye part image of the eye E to be examined introduced into the image memory 53, and the shift amounts of alignment in X, Y directions which are the left and right and up and down directions between the-center of the pupil and the measurement light axis of the eye examining portion 2 are calculated, whereafter shift is made to a step S209, where the shift amount of alignment in Z direction which is the working distance direction is calculated from the shift of the upper and lower spots on the cornea-reflected image and the X coordinates detected at the step S201.

Then, at a step S210, whether the shift amounts in X, Y directions are within the tolerance level set at the steps S204 to S207 and whether the shift amount in Z direction is within a predetermined range is determined, and if the shift amounts in X, Y and Z directions are greater than the tolerance level, shift is made to a step S211, where the up and down motor 42, the forward and backward motor 43 and the left and right motor 44 are driven according to the shift amounts to thereby make the shift of alignment small, and return is made to the step S201.

The above-described steps are repeated until at the step S210, the shift amounts are judged to be within the tolerance level, and after the completion of the automatic alignment operation, a measuring operation is performed to thereby calculate a measurement value.

The reason for setting the upper limit value is that if the tolerance level is made too wide, an accurate measurement value cannot be found stably. Also, the reason for setting the lower limit value is that if the tolerance level is made too small, too much time is required for the adjustment of alignment.

In the measurement after the alignment has been completed, the beam emitted from the measurement light source 17 is stopped down by the projection. stop 16, is primary-imaged on this side of the objective lens 12 by the projection lens 15, enters the center of the pupil of the eye E to be examined through the objective lens 12 and the dichroic mirror 11, and is imaged on the fundus Er of the eye. The reflected light from the fundus Er of the eye passes through the periphery of the pupil and again enters the objective lens 12, and becomes a thick beam and is totally reflected by the apertured mirror 13. The beam reflected on the apertured mirror 13 is divided into six by the six-division stop and also, is refracted by the six-division stop 18 and also, is refracted by the six-division prism 19 so as to be received within the proper range of the light receiving surface area of the two-dimension image pickup element 21, and six spot images are projected onto the two-dimension image pickup element 21.

The video signal of the eye fundus image picked up by the two-dimension image pickup element 21 is converted into digital data by the A/D converter 52 through the video switch 51, and is stored in the image memory 53. The CPU 41 effects the calculation of the eye refractive power on the basis of the positions of the spot images of the image stored in the image memory 53.

As described above, the ophthalmologic apparatus according to the present invention can reduce the undesirable possibility of the measuring beam being eclipsed by the iris and obtain an accurate measurement value stably even if the diameter of the pupil of the eye to be examined is small and the difference between it and the measurable minimum pupil diameter is small.

What is claimed is:

1. An ophthalmologic apparatus for effecting an alignment of an eye to be examined comprising:

an eye examining portion unit for receiving a light beam reflected from the eye to be examined and effecting a measurement of the eye to be examined;

an image pickup element for picking up an image of a front eye part of the eye to be examined; and a controller for determining whether an eyelid of the eye covers a pupil of the eye by comparing a pupil diameter of the eye obtained from an image of the eye with a predetermined value, for detecting a positional shift between a position of a vertex of a cornea of the eye and the eye examining portion unit in a case where the controller determines that the eyelid of the eye covers the pupil of the eye, for detecting the positional shift between a center of the pupil of the eye to be examined and the eye examining portion unit in a case where the controller determines that the eyelid of the eye does not cover the pupil of the eye, and for aligning the eye examining portion unit based on the detected positional shift.

2. An ophthalmologic apparatus according to claim 1, wherein the controller determines the pupil diameter of the eye to be examined on the basis of an edge of the pupil in a horizontal direction and an edge of an iris in the horizontal direction.

* * * * *